United States Patent [19]

Christensen et al.

[11] 4,262,009
[45] Apr. 14, 1981

[54] 6- AND 1,1-DISUBSTITUTED-1-CARBADETHIAPEN-2-EM-3-CARBOXYLIC ACID

[75] Inventors: Burton G. Christensen, Scotch Plains; David H. Shih, Edison, both of N.J.

[73] Assignee: Merck & Co., Inc., Rahway, N.J.

[21] Appl. No.: 99,285

[22] Filed: Dec. 3, 1979

[51] Int. Cl.³ .................... C07D 487/04; A61K 31/40
[52] U.S. Cl. ............................... 424/274; 260/239 A; 260/245.2 T
[58] Field of Search .................. 260/245.2 T; 424/274

[56] References Cited

U.S. PATENT DOCUMENTS 4,181,733  1/1980  Christensen et al. .......... 260/245.2 T Primary Examiner—Mary C. Lee
Attorney, Agent, or Firm—James A. Arno; Julian S. Levitt

[57] ABSTRACT

Disclosed are 6- and 1-substituted-1-carbadethiapen-2-em-3-carboxylic acids I of the following structure:

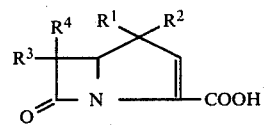

wherein $R^1$, $R^2$, $R^3$ and $R^4$ are, inter alia, independently selected from the group consisting of alkyl, aryl, and aralkyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

7 Claims, No Drawings

6- AND 1,1-DISUBSTITUTED-1-CARBADETHIAPEN-2-EM-3-CARBOXYLIC ACID

BACKGROUND OF THE INVENTION

This invention relates to 6- and 1-substituted-1-carbadethipen-2-em-3-carboxylic acids and the pharmaceutically acceptable salt, ester and amide derivatives thereof, which compounds are useful as antibiotics and which may be represented by the following generic structural formula (I):

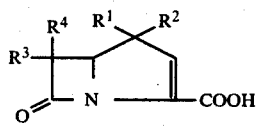

wherein $R^1$, $R^2$, $R^3$ and $R^4$ are independently selected from the group consisting of hydrogen, and substituted and unsubstituted: alkyl, cycloalkyl, spirocycloalkyl, cycloalkylalkyl, alkylcycloalkyl, aryl, aralkyl, heteroaryl, heteroaralkyl, heterocyclyl and heterocyclylalkyl wherein the substituent or substituents relative to the above named radicals are selected from the group consisting of amino, hydroxy, alkoxyl, mercapto, alkylthio, arylthio, sulfamoyl, amidino, guanidino, nitro, chloro, bromo, fluoro, cyano and carboxyl; and wherein the hetero atom in the above-named heterocyclic moiety is selected from the group consisting of oxygen, nitrogen and sulphur.

This invention also relates to the pharmaceutically acceptable salt, ester and amide derivatives of the compounds of the present invention identified by structure I, above.

This invention also relates to processes for the preparation of such compounds (I); pharmaceutical compositions comprising such compounds, and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes,* and *B. subtilis,* and gram negative bacteria such as *E. coli.* Pseudomonas, *Proteus morganii,* Serratia and Klebsiella. Further objects of this invention are to provide chemical processes for the preparation of such antibiotics and the non-toxic pharmaceutically acceptable salt, ester and amide derivatives thereof; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention I (above) are conveniently prepared by the following scheme:

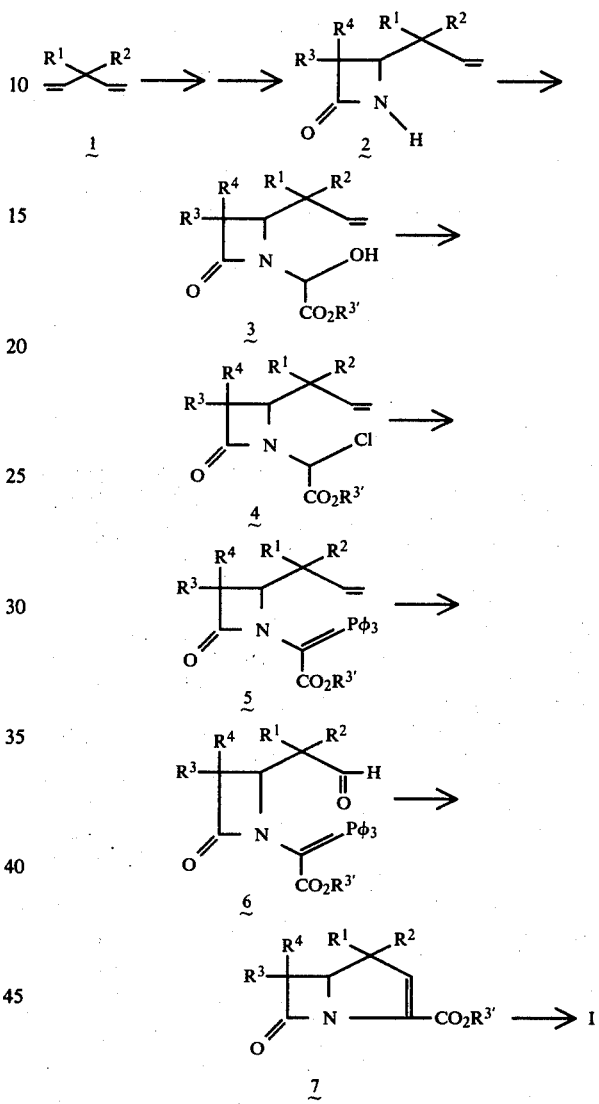

In words relative to the above diagram, the reaction 2→3 is accomplished by treating 2 in a solvent such as benzene, toluene, xylene, or the like at a temperature of from 80° to 130° C. for from 1 to 8 hours with a glyoxylate ester, $HCOCO_2R^{3'}$, wherein $R^{3'}$ is selected from the group consisting of convention protecting groups such as o-nitrobenzyl, p-nitrobenzyl, o-dinitrobenzyl, benzyl or the like. The halogenation reaction 3→4 may be conducted by any of a variety of well known halogenation means. Suitable reagents include $SOCl_2$, $POCl_3$, oxalyl chloride and the like. A preferred means of chlorination involves treating 3 in a solvent such as tetrahydrofuran (THF), ether, $CH_2Cl_2$, and the like with thionyl chloride in the presence of 1-2 equivalents (relative to the thionyl chloride) of base such as pyridine, triethylamine, quinoline and the like. Typically the reaction is conducted at a temperature of from −30° to 25° C. for from 0.5 to 1 hour. The resulting intermediate species 4 is isolated if desired by conventional procedures for later reaction, 4→5. Intermediate 5 is prepared from 4

Scharf. The following scheme summarizes the preparation of 1.

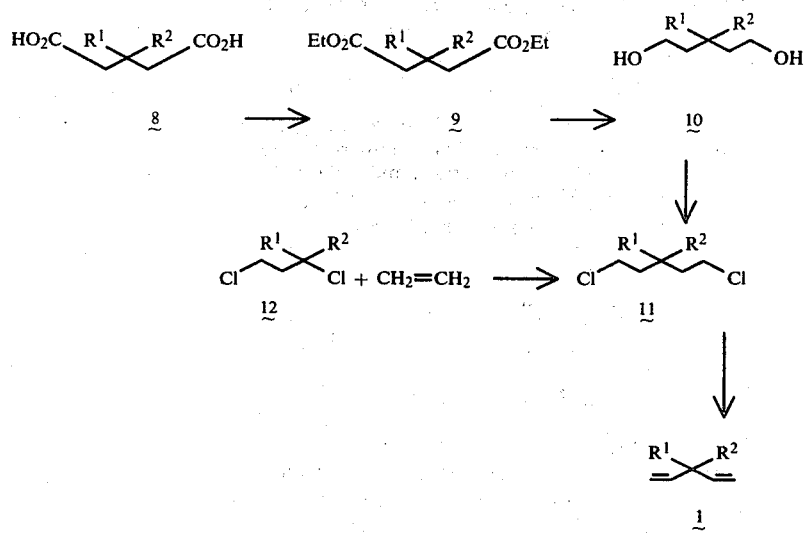

by treating 4 in a solution such as dimethylformamide (DMF), dimethylsulfoxide (DMSO), THF, dimethoxyethane (DME) or the like with 1 to 1.5 equivalents of a phosphine such as triphenylphosphine, tributylphosphine, triethylphosphine, tris-(2-cyanoethyl)phosphine or the like. Typically the reaction is conducted under a nitrogen atmosphere at a temperature of 20° to 50° C., for from 0.5 to 2 hours. The reaction 5→6 may be achieved by any of a variety of well known oxidation reagents, such as $RuO_4$, $OsO_4/NaIO_4$, $H_2O_2/Pb(OAc)_4$, or $O_3/P\phi_3$. A particularly convenient means for the oxidating 5→6 is by treating 5 with ozone in a solvent such as methanol, trifluoroacetic acid or the like at a temperature of from $-100°$ to 0° C., for from 0.1 to 4 hours, followed by treating the crude product with triphenyl phosphine at $-18°$ C. to 0° C. for from 0.1 to 2 hours. The closure step 6→7 is conducted at a temperature of from about 0° to 100° C. for from 0.25 to 24 hours in a solvent such as benzene, toluene, dioxane, xylene, or DMF. The carboxyl deblocking step 7→1 may be achieved by a number of well known procedures such as hydrolysis, hydrogenation, or photolysis of a suitable $R^{3'}$ group. Suitably hydrogenation catalysts for deblocking include the platinum metals and their oxides such as palladium on carbon and the like; suitable solvents for the hydrogenation include methanol dioxane/$H_2O$, ethanol/$H_2O$, and the like in the presence of hydrogen at a pressure of from 1 to 50 atmospheres; the hydrogenation is typically conducted for from 5 min. to 4 hours at a temperature of about 25° C. in the optional presence of a mild base such as sodium bicarbonate or the like.

Typically, however, the carboxyl blocking is achieved by photolysis of the o-nitrobenzyl ester of 7 ($R^{3'}$=o-nitrobenzyl) using 350 nm lamp in dioxane/$H_2O$ in the presence of 1-2 equivalents of $NaHCO_3$ at 25° C. for 1-6 hours.

Preparation of Starting Materials 1 and 2

With respect to starting reagent 1, its preparation is generally described in *J. Amer. Chem. Soc.*, 74 661 (1952) by E. B. Reid and T. E. Gompf, *J. Org. Chem.*, 23, 1063 (1958) by R. Ciola and K. L. Burwell, Jr., and Belgium Patent 632,193 (1963) by R. Polster and E.

In words relative to the above scheme, the diester 9 is prepared by treating the diacid 8 with thionyl chloride at reflux for two hours followed by reacting with ethanol at 80° C. for 4 hours. Reduction of the diester 9 with lithium aluminum hydride in ether at reflux for 4 hours followed by hydrolysis with 10% NaOH gives diol 10 which on further reaction with thionyl chloride gives dichloride 11. The dichloride 11 can be alternatively prepared by treating 12 with ethylene in the presence of aluminum chloride. Treatment of the dichloride 11 with base such as 2-methylquinoline, DBU or sodium hydroxide in polyethylene glycol gives the expected 3-substituted 1,4-pentadiene 1.

Preparation of 2 is summarized in the following scheme:

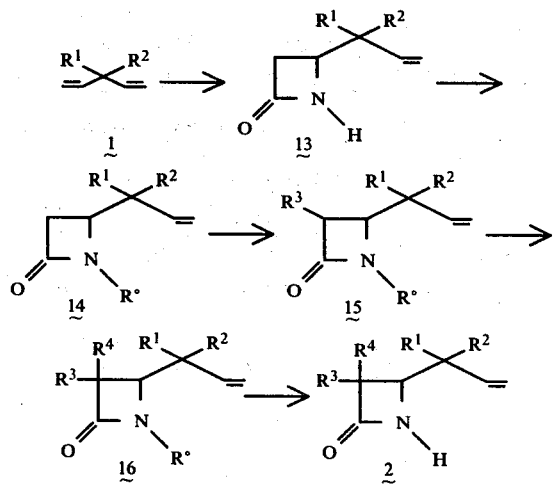

In words relative to the above scheme, the substituted azetidinone 13 is prepared by reacting a 3-substituted 1,4-pentadiene 1 with chlorosulfonylisocyanate at 25° C. to 60° C. in a pressure bottle for 3-12 days, then the resulting mixture is hydrolyzed with aqueous sodium sulfite solution between pH 6.5–7.5 at 0° C. to 25° C. for from 5 minutes to 60 minutes.

Azetidinone 13 is transformed (13→14) to establish the protecting group R° which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically R° is established by treating 13 in a solvent such as dimethylformamide, acetonitrile, hexamethylphosphoramide, tetrahydrofuran or the like with a silylating agent such as t-butyldimethylchlorosilane, t-butyldiphenylchlorosilane, triphenylchlorosilane, or the like at a temperature of from −20° to 25° C. for from 0.5 to 24 hours in the presence of a base such as triethylamine, diisopropylamine or imidazole. Alkylation of 14 provides 15. Typically, 14 is treated with a strong base such as lithium diisopropylamide, sodium hydride, phenyl lithium or butyl lithium or the like in a solvent such as tetrahydrofuran (THF), ether, dimethoxyethane or the like at a temperature of from −80° C. to 0° C., whereupon the alkylating agent of choice, $R^1X$ is added ($R^1$ is as described above and X is chloro, bromo or iodo; alternatively the alkylating agent may be $R^1$-tosylate, $R^1$-mesylate or an aldehyde or ketone such as acetaldehyde and the like) to provide mono- alkylated species 15. When desired dialkylated species 16 may be obtained from 15 by repeating the alkylating procedure 14→15. Species 2 is obtained from 15 or 16 by acid hydrolysis.

In the generic description of the present invention (I, above), the substituents $R^1$, $R^2$, $R^3$ and $R^4$ are preferably selected from the group consisting of hydrogen; substituted and unsubstituted: straight and branched loweralkyl having from 1 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl such as phenyl and naphthyl; aralkyl such as benzyl, phenethyl and the like; heterocyclyl (saturated and unsaturated) comprising mono- and bicyclic structures having from 5 to 10 ring atoms wherein one or more of the hetero atoms is selected from oxygen, nitrogen or sulphur, such as thiophene, imidazolyl, tetrazolyl, furyl and the like; heterocyclylalkyl which comprises the immediately preceding heterocyclyl moieties and the alkyl moiety comprises from 1 to 10 carbon atoms; the substituent or substituents relative to the above-named radicals are selected from the group consisting of amino, hydroxyl, cyano, carboxyl, nitro, chloro, bromo, iodo, fluoro, lower alkoxy having from 1 to 6 carbon atoms, mercapto, perhaloloweralkyl such as trifluoromethyl, loweralkylthio, guanidino, amidino, sulfamoyl, and N-substituted: sulfamoyl, amidino and guanidino wherein the N-substituent is loweralkyl having from 1 to 6 carbon atoms or aryl having 6–10 carbon atoms.

A particularly preferred class of compounds are those wherein $R^3$ is hydrogen, $R^1$ and $R^2$ are selected from the group consisting of substituted and unsubstituted: loweralkyl having from 1 to 6 carbon atoms, cyclopropyl, spirocyclopropyl, benzyl and phenyl; and $R^4$ is an α-substituted alkyl wherein the α-substituent is hydroxyl, amino or mercapto and wherein the alkyl moiety is straight or branched and comprises 1 to 6 carbon atoms; the substituents relative to the above-named preferred radicals are selected from the group consisting of hydroxyl, bromo, fluoro, chloro, iodo, amino, amidino, guanidino, phenyl, mercapto, carboxyl, trifluoromethyl, loweralkylthio and loweralkoxyl wherein the alkyl moiety of the loweralkylthio and loweralkoxyl comprises 1 to 6 carbon atoms.

Especially preferred embodiments of the present invention are those wherein $R^1$ and $R^2$ are selected from the group consisting of methyl, ethyl, propyl, isopropyl, cyclopropyl, phenyl, benzyl, 2-bromoethyl, spirocyclopropyl.

The preferred esters used as protecting groups are those wherein $R^{3'}$ is benzyl, p-nitrobenzyl, o-nitrobenzyl, t-butyl, bromo-t-butyl, t-butyl-dimethylsilyl, trimethylsilyl, trichloroethyl; or $R^{3'}$ represents pharmaceutically acceptable ester moieties such as pivaloyloxymethyl, allyl, methallyl, (2-methylthio)ethyl, 3-methyl-2-butenyl, p-t-butylbenzyl, 5-indanyl, 3-phthalidyl.

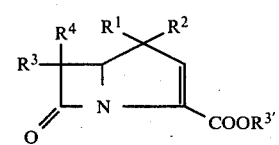

The compounds made available by the present invention are valuable antibiotics active against various gram-positive and gram-negative bacteria and, accordingly, find utility in human and veterinary medicine. Such sensitive bacteria representatively include: *Staphylococcus aureus, Escherichia coli, Klebsiella pneumoniae,* Serratia, *Salmonella typhosa,* Pseudomonas and *Bacterium proteus.* The resulting compounds may be further utilized as additives to animal feed, for preserving foodstuffs, and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

These antibiotics may be used along or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, or syrups; or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid.

Compositions for injection may be presented in unit dose form in ampules, or in multidose container. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water before use.

The compositions may also be prepared in suitable forms for absorption through the mucous membranes of the nose and throat or bronchial tissues and may conveniently take the form of powder, liquid sprays, inhalants, lozenges, or throat paints. For medication of the eyes or ears, the preparations may be presented as individual capsules, in liquid or semi-solid form, or may be used as drops. Topical applications may be formulated in hydrophobic or hydrophilic bases as ointments, creams, or lotions.

Also, in addition to a carrier, the instant compositions may include other ingredients such as stabilizers, binders, antioxidants, preservatives, lubricators, suspending agents, viscosity agents or flavoring agents and the like. In addition, there may also be included in the compositions other active ingredients to provide a broader spectrum of antibiotic activity.

For veterinary medicine the composition may, for example, be formulated as an intramammary preparation in either long or quick-release bases.

The dosage to be administered depends to a large extent upon the general health and weight of the subject being treated, and the route and frequency of administration—the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferably to employ a dosage amount in the range of from about 100 mg. to 1000 mg. In parenteral administration the unit dosage is usually the pure compound in a slightly acidified sterile water solution or in the form of a soluble powder intended for solution.

Especially preferred pharmaceutically acceptable salts and esters involving the carboxyl group of compounds of the present invention (I) are disclosed and claimed in U.S. Patent Application Ser. No. 861,314 (filed Dec. 16, 1977) now U.S. Pat. No. 4,181,733 issued Jan. 1, 1980, which application is directed, inter alia, to pharmaceutically acceptable salts and esters of the carboxyl group of thienamycin. It is precisely these salts and esters which are preferred in the present invention and they are prepared in a manner analogous to that disclosed in U.S. Patent Application Ser. No. 861,314, which is incorporated herein by reference. Thus, especially preferred salts include sodium, potassium, ammonium, and the like; and especially preferred esters include pivaloxymethyl p-t-butylbenzyl, 5-indanyl, 3-phthalidyl, 3-methyl-2-butenyl, and the like. One should note that when, in the total synthesis outlined above, $R^{3'}$ is a pharmaceutically acceptable ester moiety, there is no need for the final deblocking step if it is desired to have the final product I in the form of a pharmaceutically acceptable ester.

In the foregoing word description of the above schematic reaction diagram for the total synthesis of 6- and 1,1-disubstituted-1-carbadethiapen-2-em-3-carboxylic acids it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. All reaction temperatures are in °C.

EXAMPLE 1

Preparation of 3,3-Dimethyl-1,4-pentadiene

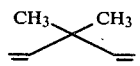

1

Procedure a

β,β-Dimethylglutaric acid (obtained from Aldrich Chemical Company) (one mole), is refluxed for 2 hours with thionyl chloride (68% excess). After removal of excess thionyl chloride, absolute ethanol (109% excess) is added slowly. The mixture is refluxed for 3 hours then distilled to collect the product, diethyl β,β-dimethylglutarate (98% yield).

To a suspension of lithium aluminum hydride (24 g) in ether (860 ml) is added dropwise with rapid stirring a solution of diethyl β,β-dimethylglutarate (124 g in 250 ml ether). The mixture is refluxed for 6 hours, then cooled to room temperature. Water (25 ml) is added slowly. The mixture is then titrated with 10% NaOH until a clear organic layer is obtained. The organic layer is separated, dried over anhydrous sodium sulfate then evaporated in vacuo to give the resulting diol as an oil (90% yield), b.p. 95° at 1.0 mm. The 3,3-dimethyl-1,5-pentanediol (0.5 mole) is treated with thionyl chloride (1.05 mole) at reflux for 3 hours. After removal of excess thionyl chloride in vacuo, the 3,3-dimethyl-1,5-dichloropentane is obtained (90% yield).

3,3-Dimethyl-1.5-dichloropentane (41 g) is added dropwise at 170° C. to a mixture of 48 g of sodium hydroxide and 40 g of polyethylene glycol tetramer and the mixture is distilled to give 3,3-dimethyl-1,4-pentadiene (66%).

Procedure b

At −40° C., 1,3-dichloro-3-methylbutane (50 g) is mixed with alumium chloride (5 g). The ethylene is bubbled through the mixture for 4 hours. The mixture is allowed to warm to room temperature and hydrolyzed with water. The mixture is extracted with ethyl acetate to give 3,3-dimethyl-1,5-dichloropentane.

A mixture of 0.5 mole of 3,3-dimethyl-1,5-dichloropentane, 2-methylquinoline (2 moles), and sodium iodide (0.1 mole) is refluxed in a flask equipped with a Vigreaux column at the top of which is a condenser and take-off. The diolefin 1 is collected during 8 hrs reaction. The product is dried over anhydrous sodium sulfate.

EXAMPLE 2

Preparation of 3-methyl-1,4-pentadiene

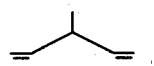

Following the procedure of Example 1(a), but replacing β,β-dimethylglutaric acid with an equivalent amount of β-methylglutaric acid, 3-methyl-1,4-pentadiene is obtained.

EXAMPLE 3

Preparation of 4-(1,1-dimethyl-pro-2-enyl)azetidin-2-one

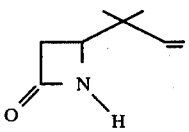

In a sealed tube, 3,3-dimethyl-1,4-pentadiene (9.6 g) and chlorosulfonyl isocyanate (14.2 g) are allowed to stand at room temperature for 6 days. The resulting mixture is diluted with methylene chloride and added slowly to a stirred aqeous solution which contains 20 g of $Na_2SO_3$ and 50 g of $K_2HPO_4$ at 0°–5° C. for 30 min. The organic layer is separated and dried over $Mg_2SO_4$. After evaporation, the crude product is chromatographed on silica gel GF eluting with EtOAc to give 3.

EXAMPLE 4

Preparation of 4-(1-methyl-pro-2-enyl)azetidin-2-one

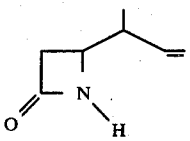

Following the procedure of Example 3, but replacing 3,3-dimethyl-1,4-pentadiene with 3-methyl-1,4-pentadiene, the title compound 4 is obtained.

EXAMPLE 5

Preparation of 5

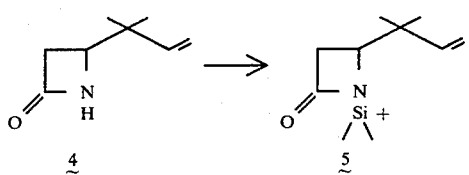

t-Butyldimethylchlorosilane (7.51 g) is added in one portion to an ice-cold, stirred solution of 4-(1,1-dimethyl-prop-2-enyl)-azetidin-2-one 4 (6.54 g) and triethylamine (5.04 g) in anhydrous dimethylformamide (100 ml). The reaction mixture is stirred at 0°–5° C. for 1 hour and then allowed to warm to room temperature. Most of the solvent is removed under vacuum to give a residue which is partitioned between diethyl ether (250 ml) and water. The ethereal phase is washed with 2.5 N hydrochloric acid (50 ml), water (3×50 ml), and brine, dried with magnesium sulfate, filtered and evaporated under vacuum to provide an oil which is purified by chromatography on silica gel (20% ether in petroleum ether) to yield 5.

EXAMPLE 6

Preparation of 6

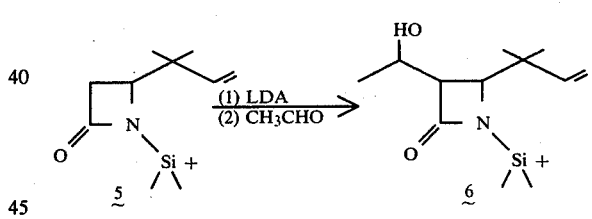

n-Butyllithium in hexane (26.25 mmol) is added slowly by syringe to a solution of diisopropylamine (26.25 mmol) in anhydrous tetrahydrofuran (100 ml) at −78° C. The resulting solution is stirred for 15 min. prior to the addition of a solution of 5 (25.0 mmol) in anhydrous tetrahydrofuran (25 ml). After stirring for 15 min. at −78° C., acetaldehyde (75 mmol) is added by syringe and the resulting solution is stirred at −78° C. for 5 min. Saturated aqueous ammonium chloride solution (15 ml) is added by syringe and the reaction mixture is allowed to warm to room temperature, then diluted with ether (250 ml) and washed with 2.5 N hydrochloric acid solution (2×50 ml), water (100 ml) and brine and dried over magnesium sulfate. Solvents are removed in vacuo and the residue is chromatographed on silica gel (1:1, ether:petroleum ether) to give the expected product 6.

EXAMPLE 7

Preparation of 7

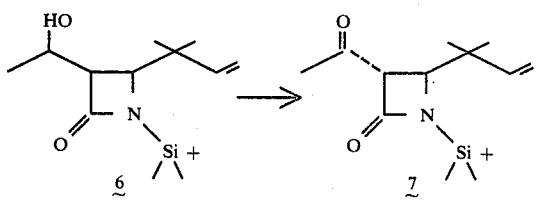

A. Trifluoroacetic anhydride (7.5 mmol) is added dropwise by syringe to a solution of dimethylsulfoxide (10 mmol) in anhydrous methylene chloride (15 ml) at −78° C. The resulting mixture is stirred at −78° C. for 20 min. A solution of 6 (5.0 mmol) in methylene chloride (15 ml) is added by syringe and the cooling bath is removed. After an additional 1 hrs., the reaction mixture is diluted with methylene chloride (100 ml), washed with water (50 ml) and brine and dried over magnesium sulfate. Removal of solvents in vacuo yields crude products which is chromatographed on silica gel (2:1, petroleum ether:ether) to yield 7.

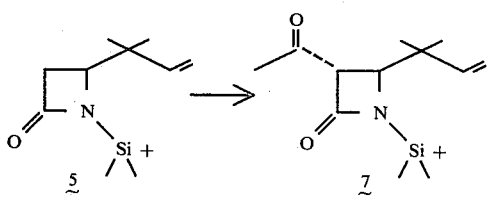

B. n-Butyllithium in hexane (4.10 mmol) is added by syringe to a solution of diisopropylamine (4.10 mmol) in anhydrous tetrahydrofuran (16 ml) at −78° C. The resulting solution is stirred at −78° C. for 15 min. prior to the addition of a solution of 1-(t-butyldimethylsilyl)-4-(1,1-dimethyl-prop-2-enyl)-azetidin-2-one 5 (2.0 mmol) in anhydrous tetrahydrofuran (2 ml). After an additional 15 min. at −78° C., the reaction mixture is added via a Teflon tube to a mixture of N-acetylimidazole (4.1 mmol) in anhydrous tetrahydrofuran (16 ml) at −78° C. The resulting yellow reaction mixture is stirred at −78° C. for 15 min., then quenched by addition of saturated aqueous ammonium chloride solution (10 ml). The reaction mixture is diluted with ether (100 ml) and washed with 2.5 N hydrochloric acid solution (25 ml) water (25 ml) and brine. The organic phase is dried over magnesium sulfate and concentrated in vacuo to yield crude products. This material is chromatographed on silica gel (2:1 petroleum ether:ether) to yield 7.

EXAMPLE 8

Preparation of 6

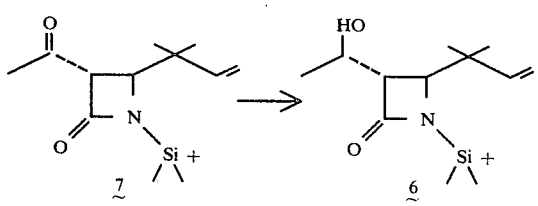

K-Selectride (potassium tri-(sec)-butylborohydride) in tetrahydrofuran (4.8 mmol) is added by syringe to a mixture of potassium iodide (2.0 mmol) and 7 (2.0 mmol) in anhydrous ether (20 ml) at room temperature. The resulting mixture is stirred at room temperature for 2.5 hours, then quenched by addition of glacial acetic acid (9.6 mmol). The resulting mixture is diluted with ethylacetate (100 ml) and filtered through celite. Removal of solvents in vacuo gives crude products which is chromatographed on silica gel (1:1 ether:petroleum ether) to yield 1.90 g (95%) of 6.

EXAMPLE 9

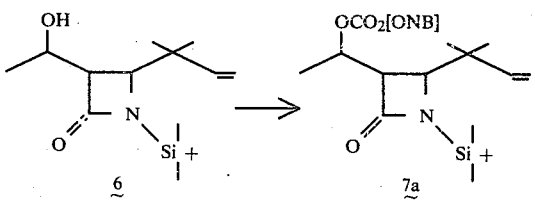

ONB = o-nitrobenzyl

Under anhydrous conditions at 0° C. a solution of 6 (3.50 g) in 60 ml methylene chloride is treated with 4-dimethylaminopyridine (3.32 g) and o-nitrobenzylchloroformate (5.88 g). The mixture is allowed to warm to room temperature and stirred for 1 hr. The resulting mixture is washed with 0.1 N HCl, water, brine and water. The organic layer is separated, dried over Na$_2$SO$_4$ and allowed to evaporate in vacuo to give crude products. The crude products, dissolved in 20 ml ether and chilled at −5° C., give the o-nitrobenzyl alcohol (0.5 g) which is separated by filtration. Purification by HPLC (silica gel) eluting with 40% ethylacetate/cyclohexane to gives 7a.

EXAMPLE 10

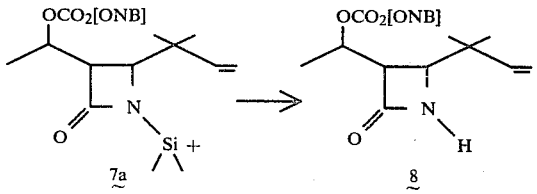

A solution of 7a (1.0 mol) in 20 ml of 9:1 (v/v) methanol-water is cooled to 0° C. Concentrated hydrochloric acid (0.34 ml) is added and the resulting solution is stirred at 0° C. for 15 min., then allowed to warm to room temperature. After 2.5 hrs, at room temperature the reaction mixture is diluted with ethyl acetate (25 ml), washed with water (10 ml) and brine, dried over magnesium sulfate and concentrated in vacuo to yield 8.

EXAMPLE 11

Preparation of 9

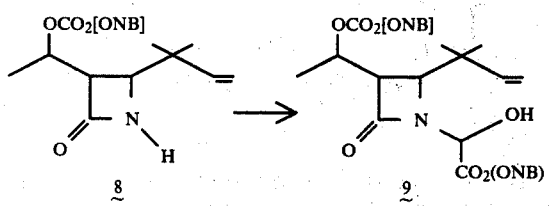

The azetidinone 8 (1.3 g) and o-nitrobenzyl glyoxylate hydrate (1.5 g) are refluxed in benzene (100 ml) for 6 hrs. The reaction apparatus is equipped with a Dean-Stark trap for removing water azeotropically. The solution is cooled, evaporated, and chromatographed on silica gel and eluted with 50% EtOAc/cyclohexane to give product.

EXAMPLE 12

Preparation of 11

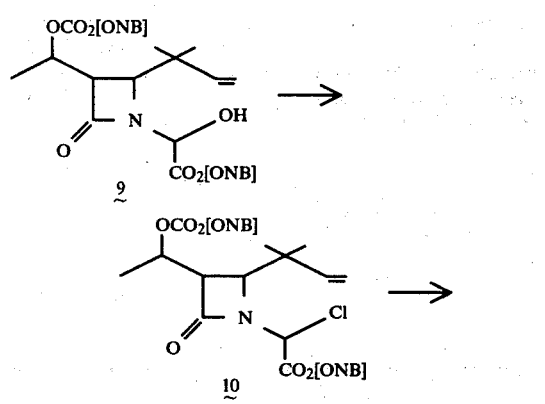

Under $N_2$, at $-20°$ C., the carbinol 9 (0.82 g) in 5 ml THF is treated with thionyl chloride (204 mg) and pyridine (136 mg) for 10 min., then the mixture is allowed to warm to room temperature. The mixture is diluted with 10 ml benzene and filtered from solids. Evaporation of filtrate in vacuo gives the expected chloride which is then treated with triphenylphosphine (468 mg) in 5 ml DMF and stirred at room temperature for 1 hr. After evaporation of solvent in vacuo, the residue is dissolved in 70 ml $CH_2Cl_2$ and washed with 0.5 M sodium phosphate buffer (pH 6.9). The organic layer is separated, dried over $MgSO_4$ and chromatographed on silica gel eluting with 30% ethylacetate/$CH_2Cl_2$ to give 11.

EXAMPLE 13

Preparation of 13

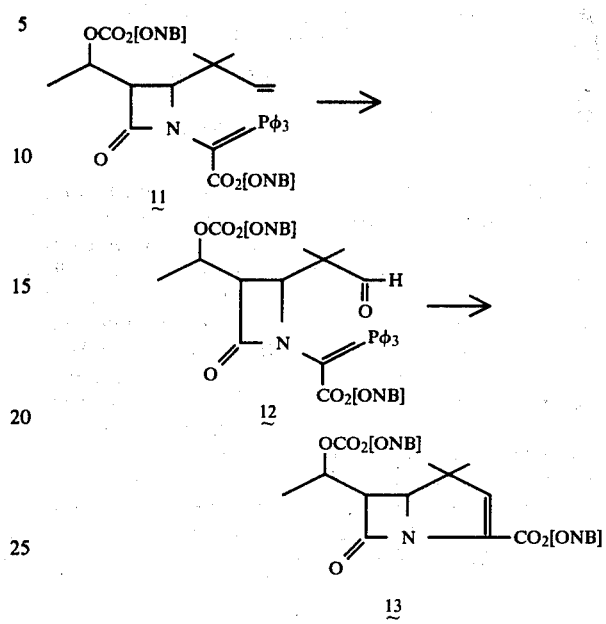

The ylide 11 (9.6 mg in 0.7 ml ethyl acetate) is mixed with trifluoroacetic acid (16 mg) and cooled to $-78°$ C. Ozone is bubbled through the mixture until it is pale blue in color. Triphenylphosphine (3.7 mg) is added and nitrogen bubbled through the mixture for 10 minutes. The flask is transferred to an ice-bath and a saturated aqueous $NaHCO_3$ solution (1.0 ml) is added. After the mixture is stirred for 30 minutes, under $N_2$, the organic layer is separated, dried over $MgSO_4$. The solution is left to stand at room temperature overnight, then evaporated and chromatographed on silica gel eluting with 50% EtOAc/cyclohexane to give 13.

EXAMPLE 14

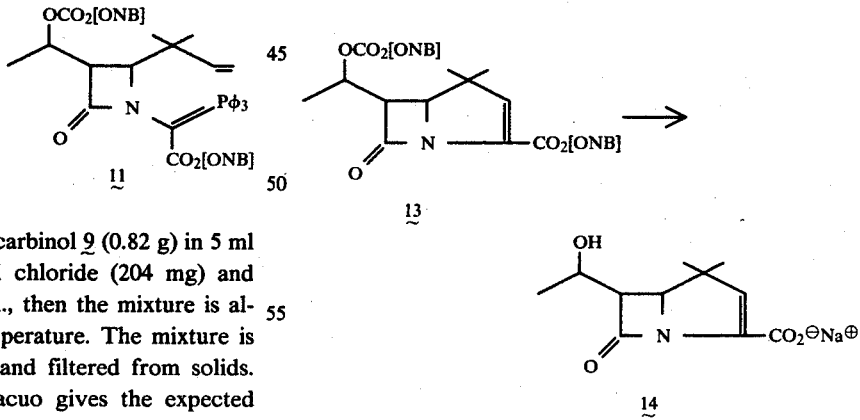

A mixture of 13 (10 mg) and 10% Pd/C (10 mg) in tetrahydrofuran (2 ml), 0.1 M dipotassium hydrogen phosphate solution (1.4 ml) and 2-propanol (0.2 ml) is hydrogenated at 40 psi on the Parr shaker for 30 minutes. The mixture is then filtered and the catalyst is washed with water. The combined filtrate and washings are extracted with ethyl acetate-ethyl ether then concentrated to $\sim 3$ ml and lyophilized to give 14.

EXAMPLE 15

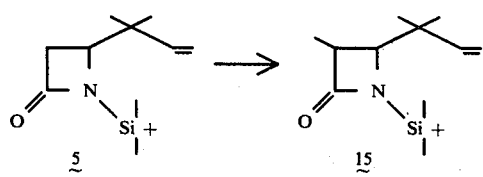

THF, 20 ml, is placed under $N_2$, treated with 1.54 ml diisopropylamine and cooled to $-78°$ C. A solution of n-butyl lithium 1.97 M in hexane (5.6 ml) is added dropwise over 5 min. The reaction mixture is stirred at $-78°$ C. for 10 min and then treated with 5 (2.14 g) in 15 ml THF which is added dropwise over 5 min. After another 10 min hexamethylphosphoramide (1.97 ml) is added. The mixture is stirred another 10 min, then treated with 2 ml of methyl iodide. The reaction mixture is stirred at $-78°$ C. for 15 min and allowed to warm to 25° C. and stirred for 15 min. The reaction mixture is diluted with EtOAc, washed once with pH 7 phosphate buffer then dried and evaporated. The residue is chromatographed on slica gel using 25% EtOAc/$C_6H_6$ as eluant to give 15.

EXAMPLE 16

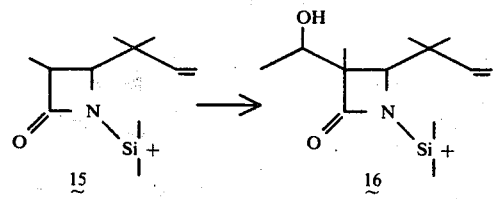

To a solution of 1.1 equivalents of freshly prepared lithium diisopropylamide in anhydrous tetrahydrofuran under a nitrogen atmosphere at $-78°$ is added a solution of 15 in anhydrous tetrahydrofuran which has been cooled to $-78°$ C. After two minutes, the resulting lithium enolate is treated with 3 equivalents of acetaldehyde. The solution is stirred for 30 minutes at $-78°$ C. and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethylacetate/benzene gives 16.

EXAMPLE 17

Following the procedure of the foregoing Examples, the following substituted azetidinones useful in the preparation of the compound of the present invention are obtained when the suggested substitution of reagents is made.

| Compound | $R^1$ | $R^2$ | $R^3$ | $R^4$ |
|---|---|---|---|---|
| (1.) | $CH_3$ | $CH_3$ | H | 2-$NO_2$-$C_6H_4$-$CH_2OC(O)OCH_2$— |
| (2.) | $CH_3$ | Et | H | $CH_3$ |
| (3.) | $CH_3$ | cyclopropyl | H | $C_6H_5C(O)$ |
| (4.) | $CH_3$ | $C_6H_5CH_2$ | H | $CH_3C(O)$ |
| (5.) | $CH_3$ | $CH(CH_3)_2$ | H | $C(CH_3)_2OH$ |
| (6.) | $CH_3$ | Ph | H | $CH(CH_3)N_3$ |
| (7.) | $CH_3$ | $CH_3CH_2CH_2$ | $CH_3$ | $CH(CH_3)OCO_2CH_2$-(2-$NO_2$-$C_6H_4$) |
| (8.) | Et | Et | $CH_3CH_2$ | $CH_2OCO_2CH_2$-(3-$NO_2$-$C_6H_4$) |
| (9.) | $CH_3$ | H | $CH_3$ | $CH_3C(O)$ |

-continued

![Structure with R1, R2, R3, R4 and NH, C=O]

| Compound | R¹ | R² | R³ | R⁴ |
|---|---|---|---|---|
| (10.) | Et | CH₃ | H | ![2-nitrophenyl OCO₂CH₂ group with isopropyl] |
| (11.) | Et | Et | CH₃ | ![2-nitrophenyl OCO₂CH₂ group with isopropyl] |
| (12.) | cyclopropyl | CH₃ | CH₃ | ![2-nitrophenyl OCO₂CH₂ group with sec-butyl] |
| (13.) | CH₃ | CH₃ | H | ![2-nitrophenyl OCO₂CH₂ group with CH₂...CH₂− ring] |
| (14.) | CH₃ | Et | H | OCH₂SCH₃ (isopropyl) |
| (15.) | H | cyclopropyl | H | ![2-nitrophenyl OCO₂CO₂CH₂ group with Ph-substituted isopropyl] |
| (16.) | isopropyl (CH₃)₂CH— | CH₃ | H | Ph— |
| (17.) | CH₃ | CH₃ | H | ![4-pyridyl] |
| (18.) | CH₃ | H | H | ![4-pyridyl] |
| (19.) | CH₃ | Et | H | ![2-nitrophenyl SCO₂CH₂ group with isopropyl (CH₃)] |
| (20.) | R¹ + R² = SPIROCYCLOPROPYL | | H | OCO₂PNB (isopropyl)<br>[PNB = p-nitrobenzyl] |
| (21.) | CH₂CH₂Br | CH₃ | H | OCO₂PNB (isopropyl) |

EXAMPLE 18

Following the foregoing text and Examples, the following species (I) are obtained by analogy when the indicated substitution from Example 17 is made in Example 11 and the resulting product carried through the procedures of Examples 12–14.

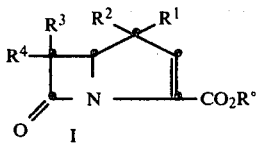

| Compound | R¹ | R² | R³ | R⁴ | R° |
|---|---|---|---|---|---|
| (1.) | $CH_3$ | $—CH_3$ | H | $HOCH_2$ | $Na^+$ |
| (2.) | Et | $—CH_3$ | H | $—CH_3$ | $Na^+$ |
| (3.) | $CH_2CH_2CH_2$ | $—CH_3$ | H | (furan-2-carbonyl) | H |
| (4.) | cyclopropyl | H | H | $CH_3C(O)$— | $K^+$ |
| (5.) | cyclopropyl | $—CH_3$ | H | $(CH_3)_2C(OH)—$ | $Na^+$ |
| (6.) | $PhCH_2$ | $CH_3$ | H | $CH_3CH(N_3)—$ | $Na^+$ |
| (7.) | Ph | $CH_3$ | $—CH_3$ | $CH_3CH(OH)—$ | $—CH_2OCCMe_3$ (with C=O) |
| (8.) | $CH_3$ | $CH_3$ | $CH_3CH_2—$ | $HOCH_2—$ | H |
| (9.) | $CH_3\!\!>\!\!CH_3$ (isopropyl) | $CH_3$ | $CH_3$ | $CH_3C(O)—$ | $Na^+$ |
| (10.) | $C_4H_9$ | $CH_3CH_2$ | H | $CH_3CH(OH)—$ | $—CH_2—C_6H_4—$ |
| (11.) | Et | $CH_3CH_2$ | $CH_3$ | $CH_3CH(OH)—$ | H |
| (12.) | $CH_3$ | cyclopropyl | $CH_3$ | $HOCH_2—$ | $Na^+$ |
| (13.) | cyclohexyl | $CH_3$ | H | $CH_3CH(OH)CH_2—$ | $(C_2H_5)_4N^+$ |
| (14.) | $o\text{-}CH_2NH_2\text{-}C_6H_4$ | $CH_3$ | H | $CH_3CH(OCH_2SCH_3)—$ | H |
| (15.) | Ph | $CH_3$ | H | $PhCH(OH)—$ | $Na^+$ |
| (16.) | $CH_3$ | $CH_3CH(CH_3)—$ | H | Ph | $Na^+$ |
| (17.) | $CH_3$ | $CH_3$ | H | pyridyl | $Na^+$ |
| (18.) | Et | $CH_3$ | H | pyridyl | $Na^+$ |
| (19.) | $CH_3$ | $CH_3$ | H | $CH_3CH(SH)—$ | $K^+$ |
| (20.) | $CH_2CH_2NH_2$ | $CH_3$ | H | $CH_3CH(OH)—$ | H |
| (21.) | $CH_3$ | $CH_3$ | H | $CH_3CH(NH_2)—$ | H |
| (22.) | $R^1 + R^2$ = spirocyclopropyl | | H | $CH_3CH(OH)—$ | $Na^\oplus$ |

EXAMPLE 19

Preparation of Pharmaceutical Compositions

One such unit dosage form is prepared by mixing 120 mg. of 6-(1-hydroxyethyl)-1,1-dimethyl-1-carbadethiapen-2-em-3-carboxylic acid with 20 mg of lactose and 5 mg. of magnesium stearate. The 145 mg. mixture onto a No. 3 gelatin capsule. Similarly, by employing more of the active ingredient and less lactose, other dosage forms can be put up in No. 3 gelatin capsules and should it be necessary to mix more than 145 mg. of ingredients together larger capsules or compressed tablets can also be prepared. The following examples are illustrative of the preparation of pharmaceutical formulations:

| TABLET | PER TABLET |
|---|---|
| 6-(1-hydroxyethyl)-1, 1-dimethyl-1-carbadethiapen-2-em-3-carboxylic acid | 125 mg. |
| Cornstarch, U.S.P. | 6 mg. |

| TABLET | PER TABLET |
| --- | --- |
| Dicalcium Phosphate | 192 mg. |
| Lactose, U.S.P. | 190 mg. |
| Magnesium Stearate | balance |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
| --- | --- |
| Ampoule: | |
| 6-(1-hydroxyethyl)-1,1-dimethyl-1-carbadethiapen-2-em-3-carboxylic acid | 500 mg. |
| Sterile Water | 2 ml. |
| OPTHALMIC SOLUTION | |
| 6-(1-hydroxyethyl)-1,1-dimethyl-1-carbadethiapen-2-em-3-carboxylic acid | 100 mg. |
| Hydroxypropylmethyl cellulose | 5 mg. |
| Sterile Water to | 1 ml. |
| OTIC SOLUTION | |
| 6-(1-hydroxyethyl)-1,1-dimethyl-1-carbadethiapen-2-em-3-carboxylic acid | 100 mg. |
| Benzalkonium chloride | 0.1 mg. |
| Sterile Water to | 1 ml. |
| TOPICAL OINTMENT | |
| 6-(1-hydroxyethyl)-1,1-dimethyl-1-carbadethiapen-2-em-3-carboxylic acid | 100 mg. |
| Polyethylene Glycol 4000 U.S.P. | 400 mg. |
| Polyethylene Glycol 400 U.S.P. | 1.0 gram |

What is claimed is:

1. A compound having the structure:

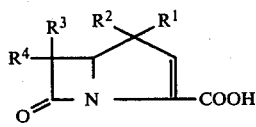

and the pharmaceutically acceptable salts thereof; wherein $R^1$, $R^2$, $R^3$ and $R^4$ are independently selected from the group consisting of hydrogen, and substituted and unsubstituted: alkyl having 1-6 carbon atoms; phenyl; phenylalkyl wherein the alkyl moiety has 1-6 carbon atoms; cycloalkyl and cycloalkylalkyl having 3 to 6 ring carbon atoms and 1-6 carbon atoms in the alkyl moiety; and spirocycloalkyl having 3 to 6 carbon atoms; wherein the substituent or substituents on $R_1$, $R^2$, $R^3$ and $R^4$ are selected from chloro, bromo, fluoro, hydroxyl, amino, mono-, di-, and trialkylamino (each alkyl having 1-6 carbon atoms), alkoxyl having 1-6 carbon atoms, cyano and carboxyl; wherein $R^1$ and $R^2$ are not hydrogen and $R^3$ and $R^4$ are not both hydrogen at the same time.

2. A compound according to claim 1 wherein $R^1$ and $R^2$ are selected from: alkyl, cyclopropyl, spirocyclopropyl, and benzyl and phenyl; $R^4$ is alkyl and phenylalkyl substituted by hydroxyl or amino; and $R^3$ is hydrogen or alkyl or phenylalkyl substituted by hydroxyl or amino.

3. A compound according to claim 2 wherein $R^1$ and $R^2$ are selected from: methyl, ethyl, isopropyl, t-butyl, spirocyclopropyl, or phenyl; $R^4$ is 1-hydroxyethyl, methyl, or hydroxymethyl; and $R^3$ is hydrogen.

4. A compound according to claim 1 having the structure:

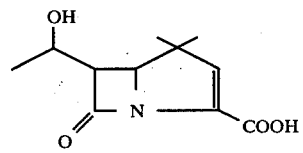

5. A compound according to claim 1 having the structure:

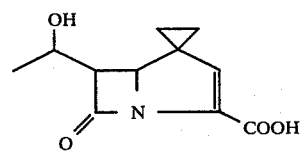

6. An antibiotic pharmaceutical composition comprising a therapeutically effective amount of a compound according to claim 1, 2, 3, 4 or 5 and a pharmaceutical carrier therefor.

7. A method of treatment comprising administering an antibiotically effective amount of a compound according to claims 1, 2, 3, 4 or 5.

* * * * *